(12) United States Patent
Mertens

(10) Patent No.: US 7,459,136 B2
(45) Date of Patent: Dec. 2, 2008

(54) PROCESS FOR MANUFACTURE OF SILICOALUMINOPHOSPHATE MOLECULAR SIEVES

(75) Inventor: Machteld Maria Mertens, Boortmeerbeek (BE)

(73) Assignee: ExxonMobile Chemical Patents Inc., Houston, TX (US)

( * ) Notice: Subject to any disclaimer, the term of this patent is extended or adjusted under 35 U.S.C. 154(b) by 695 days.

(21) Appl. No.: 11/221,192

(22) Filed: Sep. 7, 2005

(65) Prior Publication Data

US 2006/0293547 A1    Dec. 28, 2006

Related U.S. Application Data

(60) Provisional application No. 60/693,692, filed on Jun. 24, 2005.

(51) Int. Cl.
*C01B 39/54*    (2006.01)
*B01J 27/182*   (2006.01)
*C07C 1/20*     (2006.01)

(52) U.S. Cl. .............................. 423/306; 423/DIG. 30; 502/214; 585/638; 585/640

(58) Field of Classification Search ............... 423/306, 423/DIG. 30; 502/214; 585/638, 640
See application file for complete search history.

(56) References Cited

U.S. PATENT DOCUMENTS

| | | | |
|---|---|---|---|
| 4,440,871 A | 4/1984 | Lok et al. ................... 502/214 |
| 5,279,810 A | 1/1994 | Calabro ....................... 423/701 |
| 6,773,688 B2 | 8/2004 | Mertens et al. ............. 423/306 |
| 7,067,095 B1 * | 6/2006 | Mertens ....................... 423/306 |
| 7,090,814 B2 * | 8/2006 | Mertens et al. ............. 423/306 |
| 2002/0165090 A1 | 11/2002 | Janssen et al. ............... 502/214 |
| 2003/0100810 A1 | 5/2003 | Mertens et al. |
| 2003/0104931 A1 | 6/2003 | Mertens et al. |
| 2004/0241072 A1 | 12/2004 | Mertens et al. ............. 423/306 |
| 2005/0096214 A1 | 5/2005 | Janssen et al. ............... 502/214 |
| 2005/0233895 A1 * | 10/2005 | Mertens et al. ............. 502/214 |

FOREIGN PATENT DOCUMENTS

| | | |
|---|---|---|
| WO | WO 98/15496 | 4/1998 |
| WO | WO 2003/048043 | 6/2003 |

OTHER PUBLICATIONS

J. Chen et al, "Understanding the Bronsted Acidity of SAPO-5, SAPO-17, SAPO-18 and SAPO-34 and their Catalytic Performance for Methanol Conversion to Hydrocarbons", Studies in Surface Science and Catalysis, vol. 84, pp. 1731-1738 (1994).
J. Chen et al, "SAPO-18 Catalysts and Their Bronsted Acid Sites", J. Phys. Chem. 1994, vol. 98, pp. 10216-10224.
J. Chen et al, "Silicoaluminophosphate Number Eighteen (SAPO-18): A New Microporous Solid Acid Catalyst", Catalysis Letters 28, pp. 241-248 (1994).
A.M. Prakash et al, "Synthesis of SAPO-34: High Silicon Incorporation in the Presence o f Morpholine as Template", J. Chem. Soc. Faraday Trans. 1994, 90(15), pp. 2291-2296.
Yan Xu et al, "The Synthesis of SAPO-34 and CoSAPO-34 from a Triethylamine-Hydrofluoric Acid-Water System", J. Chem. Soc. Faraday Trans., 1990, 86(2), pp. 425-429.

\* cited by examiner

*Primary Examiner*—David M Brunsman

(57) ABSTRACT

A process for manufacturing a silicoaluminophosphate molecular sieve, the process comprising the steps of: (a) dissolving a silicon source into in a template at conditions sufficient to form a solution having a silicon concentration of at least 0.05 wt. %; (b) adding at least one aluminium source and at least one phosphorus source to at least a portion of the solution of step (a) to form a synthesis mixture, wherein at least the major portion of the aluminum source and phosphorus source are added to the solution after the solution has reached a dissolved silicon concentration of at least 0.03 wt. %; and (c) treating the synthesis mixture for a period of time with mixing and at a temperature sufficient to form the silicoaluminophosphate molecular sieve, wherein the silicoaluminophosphate molecular sieve comprises at least one intergrown phase of molecular sieves having AEI and CHA framework types, wherein the intergrown phase has an AEI/CHA mass ratio of from about 5/95 to 40/60 as determined by DIFFaX analysis.

45 Claims, No Drawings

PROCESS FOR MANUFACTURE OF SILICOALUMINOPHOSPHATE MOLECULAR SIEVES

CROSS REFERENCE TO RELATED APPLICATIONS

This application claims the benefit of U.S. Provisional Application No. 60/693,692 filed Jun. 24, 2005, the disclosure of which is fully incorporated herein by reference.

FIELD OF INVENTION

This invention relates to a process for manufacturing silicoaluminophosphate molecular sieves and their use in a process for making an olefin product by contacting these silicoaluminophosphate molecular sieves with an oxygenate feedstock. The silicoaluminophosphate molecular sieves in this invention comprise at least one intergrown phase of AEI and CHA molecular sieves.

BACKGROUND OF THE INVENTION

Silicoaluminophosphate (SAPO) molecular sieves contain a three-dimensional microporous crystal framework structure of $[SiO_2]$, $[AlO_2]$ and $[PO_2]$ corner sharing tetrahedral units. The $[PO_2]$ tetrahedral units are provided by a variety of compositions including phosphoric acid, organic phosphates such as triethyl phosphate, and aluminophosphates. The $[AlO_2]$ tetrahedral units are provided by a variety of compositions including aluminum alkoxides such as aluminum isopropoxide, aluminum phosphates, aluminum hydroxide, sodium aluminate, and pseudoboehmite. The $[SiO_2]$ tetrahedral units are provided by a variety of compositions including silica sols and silicon alkoxides such as tetraethylorthosilicate and fumed silica.

SAPO-34 and SAPO-18 have been reported as suitable catalysts for light olefin production from methanol. SAPO-34 belongs to the family of molecular sieves having the structure type of the zeolitic mineral chabazite (CHA). The preparation and characterisation of SAPO-34 has been reported in several publications, including U.S. Pat. No. 4,440,871; J. Chen et al. in "Studies in Surface Science and Catalysis", vol. 84, pp. 1731-1738; U.S. Pat. No. 5,279,810; J. Chen et al. in "Journal of Physical Chemistry", Vol. 98, pp. 10216-10224 (1994); J. Chen et al. in "Catalysis Letters", vol. 28, pp. 241-248 (1994); A. M. Prakash et al. in "Journal of the Chemical Society, Faraday Transactions" vol. 90(15), pp. 2291-2296 (1994); Yan Xu et al. in "Journal of the Chemical Society, Faraday Transactions" vol. 86(2), pp. 425-429 (1990), all of which are herein fully incorporated by reference.

WO 98/15496 relates to a molecular sieve that is a mixed phase comprising silicoaluminophosphates of AEI and CHA structure, referred to as RUW-19. RUW-19 is said to produce an X-ray diffractogram that includes peaks at the following 2θ values: 9.3-9.5, 10.4-10.6, 12.7-12.9, 13.8-14.0, 15.9-16.1, 16.7-16.9, 18.9-19.0, 20.5-10.7, 21.0-21.3, 23.7-24.0, 25.7-26.0, and 30.9-31.1. This publication suggests that RUW-19 is different from a physical mixture of SAPO-18 and SAPO-34. RUW-19 has peaks characteristic of an AEI structure type molecular sieve, except that the broad feature centered at about 16.9 (2θ) in RUW-19 replaces the pair of reflections centered at about 17.0 (2θ) in SAPO-18 or AEI. Also, RUW-19 does not have the reflections associated with SAPO-34 or CHA centered at 17.8 (2θ) and 24.8 (2θ). According to WO 98/15496, RUW-19 is suitable for the conversion of methanol to olefins. Throughout this description, the XRD reflection values are referred to as (2θ), which is synonymous to the expression "degrees 2θ."

U.S. Patent Publication Nos. 2002/0165090 and 2005/0096214 disclose a silicoaluminophosphate molecular sieve comprising at least one intergrown phase of molecular sieves having AEI and CHA framework types, wherein the intergrown phase has an AEI/CHA mass ratio of from about 5/95 to 40/60 as determined by DIFFaX analysis, using the powder X-ray diffraction pattern of a calcined sample of the silicoaluminophosphate molecular sieve. It also relates to methods for its preparation and to its use in the catalytic conversion of methanol to olefins.

U.S. Pat. No. 6,773,688 and U.S. Patent Publication No. 2004/0241072 disclose a process for manufacturing a SAPO-34 silicoaluminophosphate molecular sieve, the process comprising the steps of: (a) providing sources of aluminium, of phosphorus and of silicon, wherein the source of silicon is in solution with a water-miscible organic base; (b) forming a synthesis mixture from the sources; and (c) treating the synthesis mixture for a period of time and at a temperature sufficient to form the silicoaluminophosphate molecular sieve.

The present invention is related to a process for making a small particle size silicoaluminophosphate molecular sieve that comprises at least one intergrown phase of molecular sieves having AEI and CHA framework types, wherein the intergrown phase has an AEI/CHA mass ratio of from about 5/95 to 40/60 as determined by DIFFaX analysis, using the powder X-ray diffraction pattern of a calcined sample of the silicoaluminophosphate molecular sieve.

SUMMARY OF THE INVENTION

In one embodiment, the present invention relates to a process for manufacturing a silicoaluminophosphate molecular sieve, the process comprising the steps of:
(a) dissolving a silicon source into a solution containing a structure-directing template at conditions sufficient to establish a dissolved silicon concentration of at least 0.05 wt. %;
(b) adding at least one aluminum source and at least one phosphorus source to at least a portion of the solution of step (a) to form a synthesis mixture, wherein at least the major portion of the aluminum source and phosphorus source are added to the solution after the solution has reached a dissolved silicon concentration of at least 0.03 wt. %; and
(c) treating the synthesis mixture at a temperature sufficient to form the silicoaluminophosphate molecular sieve, wherein the silicoaluminophosphate molecular sieve comprises at least one intergrown phase of molecular sieves having AEI and CHA framework types, wherein the intergrown phase has an AEI/CHA mass ratio of from about 5/95 to 40/60 as determined by DIFFaX analysis.

In another embodiment, the present invention relates to a silicoaluminophosphate molecular sieve manufactured by a process comprising the steps of:
(a) dissolving a silicon source into a solution containing a structure-directing template at conditions sufficient to establish a dissolved silicon concentration of at least 0.05 wt. %;
(b) adding at least one aluminum source and at least one phosphorus source to at least a portion of the solution of step (a) to form a synthesis mixture, wherein at least the major portion of the aluminum source and phosphorus source are added to the solution after the solution has reached a dissolved silicon concentration of at least 0.03 wt. %; and (c) treating the synthesis mixture at a temperature sufficient to form the silicoaluminophosphate molecular sieve, wherein the silicoaluminophosphate molecular sieve comprises at least one intergrown phase of molecular sieves having AEI and CHA framework types, wherein the intergrown phase has an AEI/CHA mass ratio of from about 5/95 to 40/60 as determined by DIFFaX analysis.

In another embodiment, the present invention relates to a process for the conversion of an oxygenate to olefins in a reactor, the process comprising the steps of: (a) contacting the oxygenate under catalytic conversion conditions with the silicoaluminophosphate molecular sieve manufactured by the process of this invention; and (b) withdrawing the olefins from the reactor.

DETAILED DESCRIPTION OF THE INVENTION

Intergrown molecular sieve phases are disordered planar intergrowths of molecular sieve frameworks. Inventor refers to the "Catalog of Disordered Zeolite Structures", 2000 Edition, published by the Structure Commission of the International Zeolite Association and to the "Collection of Simulated XRD Powder Patterns for Zeolites", M. M. J. Treacy and J. B. Higgins, 2001 Edition, published on behalf of the Structure Commission of the International Zeolite Association for a detailed explanation on intergrown molecular sieve phases.

Regular crystalline solids are periodically ordered in three dimensions. Structurally disordered structures show periodic ordering in dimensions less than three, i.e., in two, one or zero dimensions. This phenomenon is called stacking disorder of structurally invariant Periodic Building Units. Crystal structures built from Periodic Building Units are called end-member structures if periodic ordering is achieved in all three dimensions. Disordered structures are those where the stacking sequence of the Periodic Building Units deviates from periodic ordering up to statistic stacking sequences.

The molecular sieves of the present invention are disordered planar intergrowths of end-member structures AEI and CHA. We refer to A. Simmen et al. in Zeolites (1991), vol. 11, pp. 654-661 describing the structure of molecular sieves with AEI and CHA framework types. For AEI and CHA, the Periodic Building Unit is a double six-ring layer. There are two types of layers "a" and "b", which are identical except "b" is the mirror image of "a" (180° rotation about the plane normal or mirror operation perpendicular to the plane normal). When layers of the same type stack on top of one another, i.e., aaa or bbb, the framework type CHA is generated. When layers "a" and "b" alternate, i.e., abab, the framework type AEI is generated. The molecular sieves of the present invention are made of stackings of layers "a" and "b" which contain regions of CHA framework type and regions of AEI framework type. Each change of CHA to AEI framework type is a stacking disorder or planar fault.

Preferably, the molecular sieves of the invention possess an AEI/CHA mass ratio of from about 7/93 to 38/62, more preferably from about 8/92 to 35/65, even more preferably from about 9/91 to 33/67, most preferably from about 10/90 to 30/70 as determined by DIFFaX analysis, using the powder X-ray diffraction (XRD) pattern of a calcined sample of the silicoaluminophosphate molecular sieve.

The X-ray diffraction data referred to herein are collected with a SCINTAG X2 X-Ray Powder Diffractometer (Scintag Inc., USA), using copper K-alpha radiation. The diffraction data are recorded by step-scanning at 0.02 degrees of two-theta, where theta is the Bragg angle, and a counting time of 1 second for each step. Prior to recording of each experimental X-ray diffraction pattern, the sample must be in the anhydrous state and free of any template used in its synthesis, since the simulated patterns are calculated using only framework atoms, not water or template. Given the sensitivity of silicoaluminophosphate materials to water at recording temperatures, the molecular sieve samples are calcined after preparation and kept moisture-free according to the following procedure.

About 2 grams of each molecular sieve sample are heated in an oven from room temperature under a flow of nitrogen at a rate of 3° C./minute to 200° C. and, while retaining the nitrogen flow, the sample is held at 200° C. for 30 minutes and the temperature of the oven is then raised at a rate of 2° C./minute to 650° C. The sample is then retained at 650° C. for 8 hours, the first 5 hours being under nitrogen and the final 3 hours being under air. The oven is then cooled to 200° C. at 30° C./minute and, when the XRD pattern is to be recorded, the sample is transferred from the oven directly to a sample holder and covered with Mylar foil to prevent rehydration. It is also possible after cool-down to room temperature, to do a fast recording of the XRD pattern immediately after removal of the Mylar foil (e.g. by using a total scan time of less than 5 minutes).

In the case of crystals with planar faults, interpretation of XRD diffraction patterns requires an ability to simulate the effects of stacking disorder. DIFFaX is a computer program based on a mathematical model for calculating intensities from crystals containing planar faults (see M. M. J. Tracey et al., Proceedings of the Royal Chemical Society, London, A (1991), vol. 433, pp. 499-520). DIFFaX is the simulation program selected by and available from the International Zeolite Association to simulate the XRD powder patterns for intergrown phases of zeolites (see "Collection of Simulated XRD Powder Patterns for Zeolites" by M. M. J. Treacy and J. B. Higgins, 2001, Fourth Edition, published on behalf of the Structure Commission of the International Zeolite Association). It has also been used to theoretically study intergrown phases of AEI, CHA, and KFI, as reported by K. P. Lillerud et al. in "Studies in Surface Science and Catalysis", 1994, vol. 84, pp. 543-550. DIFFaX is a well-known and established method to characterise crystalline materials with planar faults such as the intergrown molecular sieves of the present invention.

As the ratio of AEI increases relative to CHA in the intergrown phase, one can observe a decrease in intensity of certain peaks, for example, the peak at about $2\theta=25.0$ and an increase in intensity of other peaks, for example the peak at about $2\theta=17.05$ and the shoulder at $2\theta=21.2$. Intergrown phases with AEI/CHA ratios of 50/50 and above (AEI/CHA$\geq$1.0) show a broad feature centered at about 16.9 ($2\theta$).

The silicoaluminophosphates of the present invention are characterised by powder XRD diffraction patterns obtained from samples after calcination and avoiding re-hydration after calcination, having at least the reflections in the 5 to 25 ($2\theta$) range as shown in Table 1:

TABLE 1

| $2\theta$ (CuK$\alpha$) |
|---|
| 9.3-9.6 |
| 12.7-13.0 |
| 13.8-14.0 |
| 15.9-16.1 |

TABLE 1-continued

| 2θ (CuKα) |
|---|
| 17.7-18.1 |
| 18.9-19.1 |
| 20.5-20.7 |
| 23.7-24.0 |

The XRD diffraction patterns of the intergrown phases of AEI/CHA according to the present invention are also characterised by the absence of peaks in the 9.8 to 12.0 (2θ) range and the absence of any broad feature centered at about 16.9 (2θ). A further characteristic is the presence of a peak in the 17.7 to 18.1 (2θ) range. The reflection peak in the 17.7-18.1 (2θ) range has a relative intensity between 0.09 and 0.4, preferably between 0.1 and 0.35 with respect to the reflection peak at 17.9 (2θ) in the diffraction pattern of SAPO-34, all diffraction patterns being normalised to the intensity value of the reflection peak in the 20.5-20.7 (2θ) range.

The silicoaluminophosphate molecular sieves of the present invention comprise at least one intergrown phase of AEI and CHA molecular sieves. Preferably the CHA molecular sieve is SAPO-34 and the AEI molecular sieve is selected from SAPO-18, ALPO-18 or a mixture of SAPO-18 and ALPO-18. Preferably, the silicoaluminophosphates of the present invention have a silica to alumina molar ratios ($SiO_2/Al_2O_3$) ranging from 0.01 to 0.28, more preferably from 0.02 to 0.20, even more preferably from 0.03 to 0.19, most preferably from 0.03 to 0.08. The silica to alumina molar ratio ($SiO_2/Al_2O_3$) is preferably determined by chemical analysis.

The invention also provides a silicoaluminophosphate molecular sieve, especially crystalline silicoaluminophosphate molecular sieve with at least intergrown phase of AEI and CHA molecular sieves, the mean particle size of the molecular sieve being at most 600 nm, preferably at most 200 nm, preferably at most 100 nm. In another embodiment, this invention provides a silicoaluminophosphate molecular sieve, especially crystalline silicoaluminophosphate molecular sieve with at least intergrown phase of AEI and CHA molecular sieves, the mean particle size of the molecular sieve being at most 50 nm. The molecular sieve is preferably one obtainable by, and preferably is obtained by, the process of the invention. The mean particle size is measured by inspection of scanning electron micrographs (SEM's), the largest dimension of each particle being taken.

The particle size of the silicoaluminophosphate molecular sieve with at least intergrown phase of AEI and CHA molecular sieves in this invention is such that at least 50%, and preferably at least 90%, of the crystals by number are smaller than 100 nm, preferably at least 50% of the crystals are smaller than 50 nm.

The molecular sieves of the present invention may preferably be prepared by a process that comprises:
(a) dissolving a silicon source into a solution containing a structure-directing template at conditions sufficient to establish a dissolved silicon concentration of at least 0.05 wt. %;
(b) adding at least one aluminium source and at least one phosphorus source to at least a portion of the solution of step (a) to form a synthesis mixture, wherein at least the major portion of the aluminum source and phosphorus source are added to the solution after the solution has reached a dissolved silicon concentration of at least 0.03 wt. %; and
(c) treating the synthesis mixture at a temperature sufficient to form the silicoaluminophosphate molecular sieve, wherein the mixture prepared at step b) has a molar composition within the following ranges:
$P_2O_5:Al_2O_3$ from about 0.6:1 to about 1.2:1
$SiO_2:Al_2O_3$ from about 0.005:1 to about 0.6:1
$H_2O:Al_2O_3$ from about 10:1 to about 40:1.

Preferably, the mixture prepared at step b) has a molar composition within the following ranges:
$P_2O_5:Al_2O_3$ from about 0.8:1 to about 1.1:1
$SiO_2:Al_2O_3$ from about 0.01:1 to about 0.3:1, most preferably from about 0.015:1 to about 0.28:1
$H_2O:Al_2O_3$ from about 10:1 to about 40:1.

It will be understood that the molar ratio of silica to alumina in the reaction mixture will influence the silica to alumina ratio of the molecular sieve after synthesis.

The amount of organic structure directing agent is typically such that the molar ratio of directing agent to alumina is from about 0.5 to about 1.5, preferably from about 0.6 to about 1.2, such as from about 0.7 to about 1.1.

It is believed that the crystallization process to produce the molecular sieve of the present invention proceeds through the formation of a (silico)aluminophosphate precursor, having the structure of AlPO-$H_3$, variscite or metavariscite, during heat-up of the mixture, followed by dissolution of the precursor as the molecular sieve of the invention nucleates. Among the factors which influence the crystallization process to produce molecular sieve of the invention are the rate at which the mixture is heated and the rate at which the mixture is agitated at least during formation of the precursor. In particular, crystallization of the desired molecular sieve is enhanced if the heating rate is at least 8° C./hour, such as at least 10° C./hour. Typically the heating rate is from about 10° C./hour to about 40° C./hour, such as from about 15° C./hour to about 40° C./hour.

The liquid in which the silicon source is dissolved is preferably a liquid organic base (which may be in admixture with water) or an aqueous solution of a normally solid organic base that is being used as a template in the synthesis of the molecular sieve. Other organic bases may be used, provided that they do not interfere with the structure directing properties of the organic base being used as template. Conveniently, any template that is difficulty soluble in water may be mixed with (if liquid) or dissolved in (if solid) the basic organic solvent. Heating may be necessary to effect solution of the silicon source. The amount of silicon source dissolved in the solution is sufficient to establish a dissolved silicon concentration of at least 0.5 wt. %, preferably at least 1.0 wt. %, more preferably at least 1.5 wt. %, even more preferably at least 0.05 wt. %.

It is preferred that substantially all silicon source is dissolved in the solvent. The solution of step (a) is preferably substantially free of undissolved silicon source, i.e., less than 1 wt. %, preferably, less than 0.05 wt. %, more preferably less than 0.02 wt. %, even more preferably less than 0.01 wt. % of undissolved silicon in the solution.

At least one aluminium source and at least one phosphorus source is added to at least a portion of the solution of step (a) to form a synthesis mixture, wherein at least the major portion of the aluminum source and phosphorus source are added to the solution after the solution of step (a) has reached a dissolved silicon concentration of at least 0.01 wt. %, preferably 0.02 wt. %, more preferably 0.03 wt. %, even more preferably 0.05 wt. %.

Although the invention is not to be regarded as limited by any theory, it is believed that the reduction in product particle size achieved by the process of the invention may be attributable to the pre-dissolution of the silicon source providing an increased number of nucleation sites from commencement of molecular sieve crystal formation in the synthesis mixture.

In one embodiment, the heating step (a) has a temperature range having a lower limit of about 50° C. and an upper limit of about 5° C. lower than the decomposition temperature of the template, preferably a temperature range from 50° C. to 270° C., more preferably a temperature range from 70° C. to 250° C., even more preferably a temperature range from 100° C. to 200° C., most preferably a temperature range from 110° C. to 150° C.

The term "decomposition temperature" of the template as used herein means the temperature when the template irreversibly changes its chemical structure. For example, the tetraethylammonium hydroxide decomposes into water, ammonia, and olefins.

In one embodiment, the heating step (a) has a duration sufficient to dissolve substantially all silicon source in the solution, preferably at least 10 minutes, more preferably at least 30 minutes, even preferably at least 45 minutes.

In general, the treatment of the synthesis mixture to yield the desired crystalline molecular sieve, usually termed hydrothermal treatment, is preferably carried out under autogenous pressure, for example in an autoclave, for example a stainless steel autoclave which may, if desired, be preferably lined. The treatment may, for example, be carried out at a temperature within the range of from 50° C., preferably from 90° C., especially 120° C., to 250° C., depending on the molecular sieve being made. The treatment may, for example, be carried out for a period within the range of from 1 to 200 hours, preferably up to 100 hours, again depending on the molecular sieve being formed. The procedure may include an aging period, either at room temperature or, at a moderately elevated temperature, before the hydrothermal treatment at more elevated temperature. The latter may include a period of gradual or stepwise variation in temperature.

As source for the phosphorus in the synthesis mixture, there may be mentioned phosphoric acid, organic phosphates, e.g., triethylphosphate, and aluminophosphates.

As source for aluminum in the synthesis mixture there may be mentioned alumina hydrate, alumina, sodium aluminate, pseudoboehmite, organic aluminum sources, e.g., alkoxides, for example, aluminum isopropoxide, aluminum phosphate.

As source for silicon there may be mentioned fumed silica, e.g., that sold under the trade name Aerosil; an aqueous colloidal suspension of silica, e.g., that sold under the trade name Ludox AS40 or Ludox HS40; or organic silicon sources, e.g., a tetraalkyl orthosilicate, especially tetraethyl orthosilicate, although the invention is more especially of importance when the source of silicon is an inorganic source, it being understood that dissolution in the basic organic solvent may effect physical or chemical changes in the source as added.

In addition, the synthesis mixture will contain a structure-directing template (template), preferably an organic structure-directing agent. In general, as indicated above, these compounds are generally organic bases, especially nitrogen-containing bases, more especially amines and quaternary ammonium compounds, used either singly or in mixtures.

As structure-directing templates there may be mentioned, for example, tetraethyl ammonium compounds, cyclopentylamine, aminomethyl cyclohexane, piperidine, dimethyl cyclohexyl amine, triethylamine, cyclohexylamine, trimethyl hydroxyethylamine, morpholine, dipropylamine (DPA), pyridine, isopropylamine and mixtures thereof. Preferred templates are triethylamine, cyclohexylamine, piperidine, pyridine, isopropylamine, tetraethyl ammonium compounds, dipropylamine, and mixtures thereof. The tetraethylammonium compounds include tetraethyl ammonium hydroxide (TEAOH), and tetraethyl ammonium phosphate, fluoride, bromide, chloride, and acetate. Preferred tetraethyl ammonium compounds are the hydroxide and the phosphate. The molecular sieve structure may be effectively controlled using combinations of templates.

The treatment may be carried out with the vessel static or, preferably, with agitating including stirring or with rotating the vessel about a horizontal axis (tumbling). If desired, the synthesis mixture may be stirred or tumbled during an initial part of the heating stage, for example, from room temperature to an elevated, e.g., the final treatment, temperature, and be static for the remainder.

In one practical embodiment, the crystallization process of the invention comprises at least two stages; namely a first stage in which the (silico)aluminophosphate precursor material is produced and a second stage in which the precursor material is converted into the desired intergrown AEI/CHA framework type molecular sieve. In the first stage, the synthesis mixture is heated under agitation so as to raise its temperature at said rate of at least 8° C./hour to a first temperature of about 99° C. to about 150° C., such as about 115° C. to about 125° C. The synthesis mixture is then maintained at said first temperature, preferably with the agitation being continued, for a time, typically from about 0.5 hours to about 120 hours, to form an intermediate product mixture containing a slurry of the precursor material. The intermediate product mixture is then heated so as to raise its temperature at a rate of at least 8° C./hour, such as at a rate of from about 10° C./hour to about 40° C./hour, to a second temperature generally from about 150° C. to about 220° C., such as about 165° C. to about 190° C. This second heating step can be conducted under static conditions or with reduced agitation as compared with the first heating step. The second synthesis mixture is then maintained at said second temperature until the intergrown molecular sieve crystallizes from the mixture, which generally takes from about 2 to about 150 hours; such as from about 5 to about 100 hours, for example from about 10 to about 50 hours.

The invention also provides the use of a silicon source in the form of the silicon component in a solution, preferably a basic organic solution, in the hydrothermal synthesis of a silicoaluminophosphate molecular sieve to control the particle size of the product.

Typically, the molecular sieve product is formed as a slurry and can be recovered by standard means, such as by centrifugation or filtration. The separated molecular sieve product can also be washed, recovered by centrifugation or filtration and dried, or can be stored as an aqueous slurry.

As a result of the molecular sieve crystallisation process, the recovered molecular sieve contains within its pores at least a portion of the template used. The crystalline structure essentially wraps around the template, and the template should be removed to obtain catalytic activity. In a preferred embodiment, activation is performed in such a manner that the template is removed from the molecular sieve, leaving active catalytic sites with the microporous channels of the molecular sieve open for contact with a feedstock. The activation process is typically accomplished by calcining, or essentially heating the molecular sieve comprising the template at a temperature of from 200 to 800° C. in the presence of an oxygen-containing gas. In some cases, it may be desirable to heat the molecular sieve in an environment having a low oxygen concentration. This type of process can be used for partial or complete removal of the template from the intracrystalline pore system. In other cases, particularly with smaller templates, complete or partial removal from the sieve can be accomplished by conventional desorption processes.

Once the molecular sieve is made, it can be formulated into a catalyst by combining the molecular sieve with other materials that provide additional hardness or catalytic activity to the finished catalyst product. When combined with these other materials, the resulting composition is typically referred to as a silicoaluminophosphate catalyst, with the catalyst comprising the molecular sieve. This invention also relates to catalysts comprising the molecular sieves of this invention.

Materials that can be blended with the molecular sieve can be various inert or catalytically active materials, or various binder materials. These materials include compositions such as kaolin and other clays, various forms of rare earth metals, other non-zeolite catalyst components, zeolite catalyst components, alumina or alumina sol, titania, zirconia, quartz, silica or silica sol, and mixtures thereof. These components are also effective in reducing overall catalyst cost, acting as a thermal sink to assist in heat shielding the catalyst during regeneration, densifying the catalyst and increasing catalyst strength. When blended with non-silicoaluminophosphate molecular sieve materials, the amount of molecular sieve contained in the final catalyst product ranges from 10 to 90 wt. % of the total catalyst, preferably 20 to 70 wt. % of the total catalyst.

The molecular sieves synthesised in accordance with the present method can be used to dry gases and liquids; for selective molecular separation based on size and polar properties; as ion-exchangers; as catalysts in cracking, hydrocracking, disproportionation, alkylation, isomerization, oxidation; as chemical carriers; in gas chromatography; and in the petroleum industry to remove normal paraffins from distillates.

The silicoaluminophosphates of the present invention are particularly suited for the catalytic conversion of oxygenates to hydrocarbons. Accordingly, the present invention also relates to a method for making an olefin product from an oxygenate feedstock wherein the oxygenate feedstock is contacted with the catalyst of this invention comprising the molecular sieve of this invention under conditions effective to convert the oxygenate feedstock to olefin products. When compared to other silicoaluminophosphates under the same operating conditions, the silicoaluminophosphates of the present invention exhibit higher selectivity to light olefins, and produce fewer by-products.

In this process a feedstock containing an oxygenate contacts a catalyst comprising the molecular sieve in a reaction zone of a reactor at conditions effective to produce light olefins, particularly ethylene and propylene. Typically, the oxygenate feedstock is contacted with the catalyst containing the molecular sieve when the oxygenate is in vapour phase. Alternately, the process may be carried out in a liquid or a mixed vapour/liquid phase. When the process is carried out in a liquid phase or a mixed vapour/liquid phase, different conversions and selectivities of feed-to-product may result depending upon the catalyst and reaction conditions.

In this oxygenate conversion process, olefins can generally be produced at a wide range of temperatures. An effective operating temperature range can be from about 200° C. to 700° C. At the lower end of the temperature range, the formation of the desired olefin products may become markedly slow. At the upper end of the temperature range, the process may not form an optimum amount of product. An operating temperature of at least 300° C., and up to 525° C. is preferred.

In a preferred embodiment, it is highly desirable to operate at a temperature of at least 300° C. and a Temperature Corrected Normalised Methane Sensitivity (TCNMS) of less than about 0.016, preferably less than about 0.012, more preferably less than about 0.01. It is particularly preferred that the reaction conditions for making olefin from oxygenate comprise a WHSV of at least about 20 hr$^{-1}$ producing olefins and a TCNMS of less than about 0.016.

As used herein, TCNMS is defined as the Normalised Methane Selectivity (NMS) when the temperature is less than 400° C. The NMS is defined as the methane product yield divided by the ethylene product yield wherein each yield is measured on, or is converted to, a weight % basis. When the temperature is 400° C. or greater, the TCNMS is defined by the following equation, in which T is the average temperature within the reactor in ° C.:

$$TCNMS = \frac{NMS}{1 + (((T - 400)/400) \times 14.84)}$$

The pressure also may vary over a wide range, including autogenus pressures. Preferred pressures are in the range of about 5 kPa-a to about 5 MPa-a, with the most preferred range being of from about 50 kPa-a to about 0.5 MPa-a. The foregoing pressures are exclusive of any oxygen depleted diluent, and thus, refer to the partial pressure of the oxygenate compounds and/or mixtures thereof with feedstock.

The process can be carried out in a dynamic bed system or any system using a variety of transport beds, although a fixed bed system could be used. It is particularly desirable to operate the reaction process at high space velocities.

The process may be carried out in a batch, semi-continuous or continuous fashion. The process can be conducted in a single reaction zone or a number of reaction zones arranged in series or in parallel.

The conversion of oxygenates to produce olefins is preferably carried out in a large-scale continuous catalytic reactor. This type of reactor includes fluid bed reactors and concurrent riser reactors as described in "Free Fall Reactor," *Fluidization Engineering,* D. Kunii and O. Levenspiel, Robert E. Krieger Publishing Co. NY, 1977, incorporated in its entirety herein by reference. Additionally, countercurrent free fall reactors may be used in the conversion process. See, for example, U.S. Pat. No. 4,068,136 and "Riser Reactor", *Fluidization and Fluid-Particle Systems,* pages 48-59, F. A. Zenz and D. F. Othmo, Reinhold Publishing Corp., NY 1960, the descriptions of which are expressly incorporated herein by reference.

Any standard commercial scale reactor system can be used, for example fixed bed or moving bed systems. The commercial scale reactor systems can be operated at a weight hourly space velocity (WHSV) of from 1 hr$^{-1}$ to 1000 hr$^{-1}$. In the case of commercial scale reactors, WHSV is defined as the weight of hydrocarbon in the feedstock per hour per weight of silicoaluminophosphate molecular sieve content of the catalyst. The hydrocarbon content is the oxygenate content and the content of any hydrocarbon which may be present with the oxygenate. The silicoaluminophosphate molecular sieve content means only the silicoaluminophosphate molecular sieve portion that is contained within the catalyst. This excludes components such as binders, diluents, inerts, rare earth components, etc.

One or more inert diluents may be present in the feedstock, for example, in an amount of from 1 to 95 molar percent, based on the total number of moles of all feed and diluent components fed to the reaction zone. Typical diluents include, but are not necessarily limited to helium, argon, nitrogen, carbon monoxide, carbon dioxide, hydrogen, water, paraffins, alkanes (especially methane, ethane, and propane), alkylenes, aromatic compounds, and mixtures thereof. The preferred diluents are water and nitrogen. Water can be injected in either liquid or vapour form.

The level of conversion of the oxygenates is maintained to reduce the level of unwanted by-products. Conversion is also maintained sufficiently high to avoid the need for commercially undesirable levels of recycling of unreacted feeds. A reduction in unwanted by-products is seen when conversion moves from 100 mol. % to about 98 mol. % or less. Recycling up to as much as about 50 mol. % of the feed is preferred. Therefore, conversions levels which achieve both goals are from about 50 mol. % to about 98 mol. % and, desirably, from about 85 mol. % to about 98 mol. % . However, it is also acceptable to achieve conversion between 98 mol. % and 100 mol. % in order to simplify the recycling process. Oxygenate conversion is maintained using a number of methods familiar to persons of ordinary skill in the art. Examples include, but are not necessarily limited to, adjusting one or more of the following: the reaction temperature; pressure; flow rate (i.e., WHSV); level and degree of catalyst regeneration; amount of catalyst re-circulation; the specific reactor configuration; the feed composition; and other parameters which affect the conversion.

If regeneration is used, the molecular sieve catalyst can be continuously introduced as a moving bed to a regeneration zone where it is be regenerated, such as for example by removing carbonaceous materials or by oxidation in an oxygen-containing atmosphere. In a preferred embodiment, the catalyst is subject to a regeneration step by burning off carbonaceous deposits accumulated during the conversion reactions.

The oxygenate feedstock comprises at least one organic compound which contains at least one oxygen atom, such as aliphatic alcohols, ethers, carbonyl compounds (aldehydes, ketones, carboxylic acids, carbonates, esters and the like). When the oxygenate is an alcohol, the alcohol can include an aliphatic moiety having from 1 to 10 carbon atoms, more preferably from 1 to 4 carbon atoms. Representative alcohols include but are not necessarily limited to lower straight and branched chain aliphatic alcohols and their unsaturated counterparts. Examples of suitable oxygenate compounds include, but are not limited to: methanol; ethanol; n-propanol; isopropanol; $C_4$-$C_{20}$ alcohols; methyl ethyl ether; dimethyl ether; diethyl ether; di-isopropyl ether; formaldehyde; dimethyl carbonate; dimethyl ketone; acetic acid; and mixtures thereof. Preferred oxygenate compounds are methanol, dimethyl ether, or a mixture thereof. The most preferred oxygenate compound is methanol.

The process for making an olefin product from an oxygenate feedstock by contacting the oxygenate feedstock with a catalyst comprising a silicoaluminophosphate of the present invention has good catalytic performances, which is reflected by a selectivity to ethylene and propylene equal to or greater than 75.0%, and/or an ethylene to propylene ratio equal to or greater than 0.75 and/or a selectivity to propane equal to or lower than 1.0%.

The method of making the olefin products from an oxygenate feedstock can include the additional step of making the oxygenate feedstock from hydrocarbons such as oil, coal, tar sand, shale, biomass and natural gas. Methods for making oxygenate feedstocks are known in the art. These methods include fermentation to alcohol or ether, making synthesis gas, then converting the synthesis gas to alcohol or ether. Synthesis gas can be produced by known processes such as steam reforming, autothermal reforming and partial oxidisation.

One skilled in the art will also appreciate that the olefin products made by the oxygenate-to-olefin conversion reaction using the molecular sieve of the present invention can be polymerised to form polyolefins, particularly polyethylenes and polypropylenes. Processes for forming polyolefins from olefins are known in the art. Catalytic processes are preferred. Particularly preferred are metallocene, Ziegler/Natta and acid catalytic systems. See, for example, U.S. Pat. Nos. 3,258,455; 3,305,538; 3,364,190; 5,892,079; 4,659,685; 4,076,698; 3,645,992; 4,302,565; and 4,243,691, the catalyst and process descriptions of each being expressly incorporated herein by reference. In general, these methods involve contacting the olefin product with a polyolefin-forming catalyst at a pressure and temperature effective to form the polyolefin product.

A preferred polyolefin-forming catalyst is a metallocene catalyst as described in U.S. Pat. No. 5,324,800. The preferred temperature range of operation is between 50 and 240° C. and the reaction can be carried out at low, medium or high pressure, being anywhere within the range of about 100 to 20000 kPa-a. For processes carried out in solution, an inert diluent can be used, and the preferred operating pressure range is between 1000 and 15000 kPa-a, with a preferred temperature range of between 120 and 230° C. For gas phase processes, it is preferred that the temperature generally be within a range of 60 to 160° C., and that the operating pressure be between 500 and 5000 kPa-a.

In addition to polyolefins, numerous other olefin derivatives may be formed from the olefins recovered from this invention. These include, but are not limited to, aldehydes, alcohols, acetic acid, linear alpha olefins, vinyl acetate, ethylene dichloride and vinyl chloride, ethylbenzene, ethylene oxide, cumene, isopropyl alcohol, acrolein, allyl chloride, propylene oxide, acrylic acid, ethylene-propylene rubbers, and acrylonitrile, and trimers and dimers of ethylene, propylene or butylenes. The methods of manufacturing these derivatives are well known in the art, and therefore, are not discussed herein.

The invention further provides the products of the processes and of the uses of the earlier aspects of the invention. The products, if required after cation exchange and/or calcining, have utility as catalyst precursors, catalysts, and separation and absorption media. They are especially useful in numerous hydrocarbon conversions, separations and absorptions. They may be used alone, or in admixture with other molecular sieves, in particulate form, supported or unsupported, or in the form of a supported layer, for example in the form of a membrane, for example as described in International Application WO 94/25151. Hydrocarbon conversions include, for example, cracking, reforming, hydrofining, amortization, oligomerization, isomerization, dewaxing, and hydrocracking (e.g., naphtha to light olefins, higher to lower molecular weight hydrocarbons, alkylation, transalkylation, disproportionation or isomerization of aromatics). Other conversions include the reaction of alcohols with olefins and the conversion of oxygenates to hydrocarbons, especially of methanol to olefins, especially light olefins. SAPO-34 produced by the process of the invention is especially suitable for this conversion.

Conversion of oxygenates may be carried out with the oxygenate, e.g., methanol, in the liquid or, preferably, the vapor phase, in batch or, preferably, continuous mode. When carried out in continuous mode, a weight hourly space velocity (WHSV), based on oxygenate, of preferably 1 to 1000, preferably 1 to 100, hr$^{-1}$ may preferably be used. An elevated temperature is generally required to obtain economic conversion rates, e.g., one between 300 and 600° C., preferably from 400 to 500° C., and more preferably about 450° C. The catalyst may be in a fixed bed, or a dynamic, e.g., fluidized or moving, bed.

The oxygenate feedstock may be mixed with a diluent, inert under the reaction conditions, e.g., argon, nitrogen, carbon dioxide, hydrogen, or steam. The concentration of methanol in the feedstream may vary widely, e.g., from 5 to 90 mol. % of the feedstock. The pressure may vary within a wide range, e.g., from atmospheric to 500 kPa-a.

EXAMPLES

The following Examples, in which parts are by weight unless otherwise indicated, illustrate preferred embodiments of the invention. The source and purity of starting materials are those first given, unless indicated otherwise.

SEM was obtained on a JEOL JSM-6340F Field Emission Scanning Electron Microscope, using a magnification of 20,000 times at a voltage of 2 keV.

In these examples, the XRD diffraction patterns were recorded on a SCINTAG X2 X-Ray Powder Diffractometer (Scintag Inc. USA), using copper K$\alpha$ radiation. The molecular sieve samples were calcined after preparation and kept moisture-free according to the following procedure:

About 2 grams of molecular sieve were heated-up from room temperature to 200° C. under a flow of nitrogen at a rate of 2° C. per minute. The temperature was held at 200° C. for 30 minutes. Then the sample was heated-up from 200° C. to 650° C. under nitrogen at a rate of 2° C. per minute. The sample was held at 650° C. under nitrogen for 5 hours. Nitrogen was then replaced by air and the sample was kept at 650° C. under air for 3 hours. The sample was then cooled to 200° C. and kept at 200° C. to prevent hydration. The hot sample was then transferred into the XRD sample cup and was covered by Mylar foil to prevent hydration. XRD diffraction patterns were recorded in the 2$\theta$ range of 12 to 24 degrees.

DIFFaX analysis was used to determine the AEI/CHA mass ratio of the molecular sieves. Powder XRD diffraction patterns for varying ratios of AEI/CHA were generated using the DIFFaX program available from the International Zeolite Association (see also M. M. J. Tracey et al., Proceedings of the Royal Chemical Society, London, A (1991), vol. 433, pp. 499-520 "Collection of Simulated XRD Powder Patterns for Zeolites" by M. M. J. Treacy and J. B. Higgins, 2001, Fourth Edition, published on behalf of the Structure Commission of the International Zeolite Association). Table 2 gives the DIFFaX input file used to simulate the XRD diffraction patterns. For the purposes of this analysis, calculations were based on a random distribution of the layers. Such calculations are used for statistical purposes only, and do not mean that the true nature of the material is necessarily random. The simulation diffraction patterns were then compared with the experimental powder XRD diffraction patterns.

TABLE 2

INPUT FILE USED TO SIMULATE XRD DIFFRACTION PATTERNS WITH DIFFAX

{data File for Random AEI-CHA Intergrowths - Starting from an AEI Unit Cell}
{This file is for a 75% probability of a transition generating CHA-type cages}
{and a 25% probability of a transition generating AEI-type cages}
INSTRUMENTAL {Header for instrumental section}
X-RAY {Simulate X-ray diffraction}
1.5418 {X-ray wavelength}
PSEUDO-VOIGT 0.1 −0.036 0.009 0.6 {Instrumental broadening (much slower)}

TABLE 2-continued

INPUT FILE USED TO SIMULATE XRD DIFFRACTION PATTERNS WITH DIFFAX

STRUCTURAL {Header for structural section}
13.711 12.731 18.57 90. {unit cell coordinates a, b, c, and gamma}
UNKNOWN {P1 - all coordinates given}
2 {Layer 1 & Layer 2}
infinite {Layers are very wide in the a–b plane}

LAYER 1
NONE

| | | | | | |
|---|---|---|---|---|---|
| Al | 11 | 0.885410 | 0.951850 | 0.168520 | 1.5 | 1.0 |
| Al | 12 | 0.385410 | 0.451850 | 0.168520 | 1.5 | 1.0 |
| Al | 13 | 0.114590 | 0.048150 | −0.168520 | 1.5 | 1.0 |
| Al | 14 | 0.614590 | 0.548150 | −0.168520 | 1.5 | 1.0 |
| Al | 21 | 0.881620 | 0.230480 | −0.059470 | 1.5 | 1.0 |
| Al | 22 | 0.381620 | 0.730480 | −0.059470 | 1.5 | 1.0 |
| Al | 23 | 0.118380 | 0.769520 | 0.059470 | 1.5 | 1.0 |
| Al | 24 | 0.618380 | 0.269520 | 0.059470 | 1.5 | 1.0 |
| Al | 31 | 0.220800 | 0.094820 | 0.051200 | 1.5 | 1.0 |
| Al | 32 | 0.720800 | 0.594820 | 0.051200 | 1.5 | 1.0 |
| Al | 33 | 0.779200 | 0.905180 | −0.051200 | 1.5 | 1.0 |
| Al | 34 | 0.279200 | 0.405180 | −0.051200 | 1.5 | 1.0 |
| P | 41 | 0.779200 | 0.101060 | 0.055650 | 1.5 | 1.0 |
| P | 42 | 0.279200 | 0.601060 | 0.055650 | 1.5 | 1.0 |
| P | 43 | 0.220800 | 0.898940 | −0.055650 | 1.5 | 1.0 |
| P | 44 | 0.720800 | 0.398940 | −0.055650 | 1.5 | 1.0 |
| P | 51 | 0.113750 | 0.236960 | −0.062850 | 1.5 | 1.0 |
| P | 52 | 0.613750 | 0.736960 | −0.062850 | 1.5 | 1.0 |
| P | 53 | 0.886250 | 0.763040 | 0.062850 | 1.5 | 1.0 |
| P | 54 | 0.386250 | 0.263040 | 0.062850 | 1.5 | 1.0 |
| P | 61 | 0.119660 | 0.962530 | 0.166920 | 1.5 | 1.0 |
| P | 62 | 0.619660 | 0.462530 | 0.166920 | 1.5 | 1.0 |
| P | 63 | 0.880340 | 0.037470 | −0.166920 | 1.5 | 1.0 |
| P | 64 | 0.380340 | 0.537470 | −0.166920 | 1.5 | 1.0 |
| O | 71 | 0.168130 | 0.057460 | 0.132520 | 3.0 | 1.0 |
| O | 72 | 0.668130 | 0.557460 | 0.132520 | 3.0 | 1.0 |
| O | 73 | 0.831870 | 0.942540 | −0.132520 | 3.0 | 1.0 |
| O | 74 | 0.331870 | 0.442540 | −0.132520 | 3.0 | 1.0 |
| O | 81 | 0.141650 | 0.178130 | 0.005340 | 3.0 | 1.0 |
| O | 82 | 0.641650 | 0.678130 | 0.005340 | 3.0 | 1.0 |
| O | 83 | 0.858350 | 0.821870 | −0.005340 | 3.0 | 1.0 |
| O | 84 | 0.358350 | 0.321870 | −0.005340 | 3.0 | 1.0 |
| O | 91 | 0.005220 | 0.261180 | −0.061110 | 3.0 | 1.0 |
| O | 92 | 0.505220 | 0.761180 | −0.061110 | 3.0 | 1.0 |
| O | 93 | 0.994780 | 0.738820 | 0.061110 | 3.0 | 1.0 |
| O | 94 | 0.494780 | 0.238820 | 0.061110 | 3.0 | 1.0 |
| O | 101 | 0.850040 | 0.181060 | 0.024720 | 3.0 | 1.0 |
| O | 102 | 0.350040 | 0.681060 | 0.024720 | 3.0 | 1.0 |
| O | 103 | 0.149960 | 0.818940 | −0.024720 | 3.0 | 1.0 |
| O | 104 | 0.649960 | 0.318940 | −0.024720 | 3.0 | 1.0 |
| O | 111 | 0.824370 | 0.050450 | 0.121850 | 3.0 | 1.0 |
| O | 112 | 0.324370 | 0.550450 | 0.121850 | 3.0 | 1.0 |
| O | 113 | 0.175630 | 0.949550 | −0.121850 | 3.0 | 1.0 |
| O | 114 | 0.675630 | 0.449550 | −0.121850 | 3.0 | 1.0 |
| O | 121 | 0.009850 | 0.978500 | 0.168460 | 3.0 | 1.0 |
| O | 122 | 0.509850 | 0.478500 | 0.168460 | 3.0 | 1.0 |
| O | 123 | 0.990150 | 0.021500 | −0.168460 | 3.0 | 1.0 |
| O | 124 | 0.490150 | 0.521500 | −0.168460 | 3.0 | 1.0 |
| O | 131 | 0.144120 | 0.863920 | 0.124490 | 3.0 | 1.0 |
| O | 132 | 0.644120 | 0.363920 | 0.124490 | 3.0 | 1.0 |
| O | 133 | 0.855880 | 0.136080 | −0.124490 | 3.0 | 1.0 |
| O | 134 | 0.355880 | 0.636080 | −0.124490 | 3.0 | 1.0 |
| O | 141 | 0.329790 | 0.160550 | 0.067710 | 3.0 | 1.0 |
| O | 142 | 0.829790 | 0.660550 | 0.067710 | 3.0 | 1.0 |
| O | 143 | 0.670210 | 0.839450 | −0.067710 | 3.0 | 1.0 |
| O | 144 | 0.170210 | 0.339450 | −0.067710 | 3.0 | 1.0 |
| O | 161 | 0.814580 | 0.343580 | −0.077240 | 3.0 | 1.0 |
| O | 162 | 0.314580 | 0.843580 | −0.077240 | 3.0 | 1.0 |
| O | 163 | 0.185420 | 0.656420 | 0.077240 | 3.0 | 1.0 |
| O | 164 | 0.685420 | 0.156420 | 0.077240 | 3.0 | 1.0 |
| O | 171 | 0.136560 | 0.169180 | −0.128110 | 3.0 | 1.0 |
| O | 172 | 0.636560 | 0.669180 | −0.128110 | 3.0 | 1.0 |
| O | 173 | 0.863440 | 0.830820 | 0.128110 | 3.0 | 1.0 |
| O | 174 | 0.363440 | 0.330820 | 0.128110 | 3.0 | 1.0 |
| O | 181 | 0.243600 | 0.983110 | −0.000100 | 3.0 | 1.0 |
| O | 182 | 0.743600 | 0.483110 | −0.000100 | 3.0 | 1.0 |
| O | 183 | 0.756400 | 0.016890 | 0.000100 | 3.0 | 1.0 |

TABLE 2-continued

INPUT FILE USED TO SIMULATE XRD DIFFRACTION PATTERNS WITH DIFFAX

| | | | | | | |
|---|---|---|---|---|---|---|
| O | 184 | 0.256400 | 0.516890 | 0.000100 | 3.0 | 1.0 |
| O | 151 | 0.842490 | 0.949350 | 0.256680 | 3.0 | 1.0 |
| O | 152 | 0.342490 | 0.449350 | 0.256680 | 3.0 | 1.0 |
| O | 155 | 0.157510 | 0.949350 | 0.243320 | 3.0 | 1.0 |
| O | 156 | 0.657510 | 0.449350 | 0.243320 | 3.0 | 1.0 |

LAYER 2
NONE

| | | | | | | |
|---|---|---|---|---|---|---|
| Al | 15 | 0.114590 | 0.951850 | −0.168520 | 1.5 | 1.0 |
| Al | 16 | 0.614590 | 0.451850 | −0.168520 | 1.5 | 1.0 |
| Al | 15 | 0.885410 | 0.048150 | 0.168520 | 1.5 | 1.0 |
| Al | 18 | 0.385410 | 0.548150 | 0.168520 | 1.5 | 1.0 |
| Al | 25 | 0.118380 | 0.230480 | 0.059470 | 1.5 | 1.0 |
| Al | 26 | 0.618380 | 0.730480 | 0.059470 | 1.5 | 1.0 |
| Al | 27 | 0.881620 | 0.769520 | −0.059470 | 1.5 | 1.0 |
| Al | 28 | 0.381620 | 0.269520 | −0.059470 | 1.5 | 1.0 |
| Al | 35 | 0.779200 | 0.094820 | −0.051200 | 1.5 | 1.0 |
| Al | 36 | 0.279200 | 0.594820 | −0.051200 | 1.5 | 1.0 |
| Al | 37 | 0.220800 | 0.905180 | 0.051200 | 1.5 | 1.0 |
| Al | 38 | 0.720800 | 0.405180 | 0.051200 | 1.5 | 1.0 |
| P | 45 | 0.220800 | 0.101060 | −0.055650 | 1.5 | 1.0 |
| P | 46 | 0.720800 | 0.601060 | −0.055650 | 1.5 | 1.0 |
| P | 47 | 0.779200 | 0.898940 | 0.055650 | 1.5 | 1.0 |
| P | 48 | 0.279200 | 0.398940 | 0.055650 | 1.5 | 1.0 |
| P | 55 | 0.886250 | 0.236960 | 0.062850 | 1.5 | 1.0 |
| P | 56 | 0.386250 | 0.736960 | 0.062850 | 1.5 | 1.0 |
| P | 57 | 0.113750 | 0.763040 | −0.062850 | 1.5 | 1.0 |
| P | 58 | 0.613750 | 0.263040 | −0.062850 | 1.5 | 1.0 |
| P | 65 | 0.880340 | 0.962530 | −0.166920 | 1.5 | 1.0 |
| P | 66 | 0.380340 | 0.462530 | −0.166920 | 1.5 | 1.0 |
| P | 67 | 0.119660 | 0.037470 | 0.166920 | 1.5 | 1.0 |
| P | 68 | 0.619660 | 0.537470 | 0.166920 | 1.5 | 1.0 |
| O | 75 | 0.831870 | 0.057460 | −0.132520 | 3.0 | 1.0 |
| O | 76 | 0.331870 | 0.557460 | −0.132520 | 3.0 | 1.0 |
| O | 77 | 0.168130 | 0.942540 | 0.132520 | 3.0 | 1.0 |
| O | 78 | 0.668130 | 0.442540 | 0.132520 | 3.0 | 1.0 |
| O | 85 | 0.858350 | 0.178130 | −0.005340 | 3.0 | 1.0 |
| O | 86 | 0.358350 | 0.678130 | −0.005340 | 3.0 | 1.0 |
| O | 87 | 0.141650 | 0.821870 | 0.005340 | 3.0 | 1.0 |
| O | 88 | 0.641650 | 0.321870 | 0.005340 | 3.0 | 1.0 |
| O | 95 | 0.994780 | 0.261180 | 0.061110 | 3.0 | 1.0 |
| O | 96 | 0.494780 | 0.761180 | 0.061110 | 3.0 | 1.0 |
| O | 97 | 0.005220 | 0.738820 | −0.061110 | 3.0 | 1.0 |
| O | 98 | 0.505220 | 0.238820 | −0.061110 | 3.0 | 1.0 |
| O | 105 | 0.149960 | 0.181060 | −0.024720 | 3.0 | 1.0 |
| O | 106 | 0.649960 | 0.681060 | −0.024720 | 3.0 | 1.0 |
| O | 107 | 0.850040 | 0.818940 | 0.024720 | 3.0 | 1.0 |
| O | 108 | 0.350040 | 0.318940 | 0.024720 | 3.0 | 1.0 |
| O | 115 | 0.175630 | 0.050450 | −0.121850 | 3.0 | 1.0 |
| O | 116 | 0.675630 | 0.550450 | −0.121850 | 3.0 | 1.0 |
| O | 117 | 0.824370 | 0.949550 | 0.121850 | 3.0 | 1.0 |
| O | 118 | 0.324370 | 0.449550 | 0.121850 | 3.0 | 1.0 |
| O | 125 | 0.990150 | 0.978500 | −0.168460 | 3.0 | 1.0 |
| O | 126 | 0.490150 | 0.478500 | −0.168460 | 3.0 | 1.0 |
| O | 127 | 0.009850 | 0.021500 | 0.168460 | 3.0 | 1.0 |
| O | 128 | 0.509850 | 0.521500 | 0.168460 | 3.0 | 1.0 |
| O | 135 | 0.855880 | 0.863920 | −0.124490 | 3.0 | 1.0 |
| O | 136 | 0.355880 | 0.363920 | −0.124490 | 3.0 | 1.0 |
| O | 137 | 0.144120 | 0.136080 | 0.124490 | 3.0 | 1.0 |
| O | 138 | 0.644120 | 0.636080 | 0.124490 | 3.0 | 1.0 |
| O | 145 | 0.670210 | 0.160550 | −0.067710 | 3.0 | 1.0 |
| O | 146 | 0.170210 | 0.660550 | −0.067710 | 3.0 | 1.0 |
| O | 147 | 0.329790 | 0.839450 | 0.067710 | 3.0 | 1.0 |
| O | 148 | 0.829790 | 0.339450 | 0.067710 | 3.0 | 1.0 |
| O | 165 | 0.185420 | 0.343580 | 0.077240 | 3.0 | 1.0 |
| O | 166 | 0.685420 | 0.843580 | 0.077240 | 3.0 | 1.0 |
| O | 167 | 0.814580 | 0.656420 | −0.077240 | 3.0 | 1.0 |
| O | 168 | 0.314580 | 0.156420 | −0.077240 | 3.0 | 1.0 |
| O | 175 | 0.863440 | 0.169180 | 0.128110 | 3.0 | 1.0 |
| O | 176 | 0.363440 | 0.669180 | 0.128110 | 3.0 | 1.0 |
| O | 177 | 0.136560 | 0.830820 | −0.128110 | 3.0 | 1.0 |
| O | 178 | 0.636560 | 0.330820 | −0.128110 | 3.0 | 1.0 |
| O | 185 | 0.756400 | 0.983110 | 0.000100 | 3.0 | 1.0 |
| O | 186 | 0.256400 | 0.483110 | 0.000100 | 3.0 | 1.0 |
| O | 187 | 0.243600 | 0.016890 | −0.000100 | 3.0 | 1.0 |
| O | 188 | 0.743600 | 0.516890 | −0.000100 | 3.0 | 1.0 |
| O | 1511 | 0.157510 | 0.050650 | 0.243320 | 3.0 | 1.0 |
| O | 1512 | 0.657510 | 0.550650 | 0.243320 | 3.0 | 1.0 |
| O | 1515 | 0.842490 | 0.050650 | 0.256680 | 3.0 | 1.0 |
| O | 1516 | 0.342490 | 0.550650 | 0.256680 | 3.0 | 1.0 |

STACKING {Header for stacking description}
recursive {Statistical ensemble}
infinite {Infinite number of layers}
TRANSITIONS {Header for stacking transition data}
{Transitions from layer 1}
0.75 0.0 −0.084 0.5 {layer 1 to layer 1: CHA-type cages}
0.25 0.0 0.0 0.5 {layer 1 to layer 2: AEI-type cages}
{Transitions from layer 2}
0.25 0.0 0.0 0.5 {layer 2 to layer 1: AEI-type cages}
0.75 0.0 0.0857 0.5 {layer 2 to layer 2: CHA-type cages}

Example 1 (Comparative Example)

A synthesis mixture with the following molar ratios was prepared with the quantities indicated in table 3:

0.15 $SiO_2/Al_2O_3/P_2O_5/TEAOH/35\ H_2O$ by adding Ludox AS40 ($SiO_2$ 40 wt. % in water) to a diluted solution of phosphoric acid and TEAOH. The Condea Pural SB ($Al_2O_3$ pseudoboehmite containing 25 wt. % of water) was added to this mixture. The homogeneous slurry was heated in a stainless steel autoclave to 165° C. with a heating rate of 20° C./hr and kept at this temperature for 72 hrs. Stirring was applied during the whole hydrothermal treatment. After cooling the product was washed and dried overnight at 120° C. According to XRD, the product was an intergrown phase of molecular sieves having AEI and CHA framework types, with a particle size of 1.5 micron as measured by SEM.

TABLE 3

| Component | Proportion |
|---|---|
| Colloidal silica (Ludox AS40) 40 wt. % in water | 37.25 |
| TEAOH, (Eastern Chemical) 35 wt. % in water | 702.04 |
| $Al_2O_3$ (Condea Pural SB) | 227.01 |
| $H_3PO_4$ (Acros), 85 wt. % in water | 384.71 |
| Water | 369.85 |

Example 2

A synthesis mixture with the same molar ratios as the example 1 was prepared with the quantities indicated in table 4.

TABLE 4

| Component | Proportion |
|---|---|
| Colloidal silica (Ludox AS40) 40 wt. % in water | 16.56 |
| TEAOH, (Eastern Chemical) 35 wt. % in water | 306.35 |
| $Al_2O_3$ (Condea Pural SB) | 99.04 |

TABLE 4-continued

| Component | Proportion |
|---|---|
| H$_3$PO$_4$ (Acros), 85 wt. % in water | 167.37 |
| Water | 160.68 |

A mixture of the TEAOH and Ludox was heated for 12 hrs at 120° C. under autogenous pressure. After cooling this solution to room temperature, the phosphoric acid was added to this solution. After the solution was homogeneous, the Condea Pural SB alumina was added and the mixture was stirred until homogeneous. This mixture was heated to 170° C. with a heating rate of 20° C./hr and kept at this temperature for 48 hrs. The mixture was stirred during the whole hydrothermal treatment at a tip-speed of 0.9 m/s. After cooling the product was washed and dried overnight at 120° C. According to XRD, the product was an intergrown phase of molecular sieves having AEI and CHA framework types with a particle size smaller than 500 nm as measured by SEM.

Example 3

A synthesis mixture with the same molar ratios as the example 2 was prepared with the quantities indicated in table 5.

TABLE 5

| Component | Quantity (gram) |
|---|---|
| Colloidal silica (Ludox AS40) 40 wt. % in water | 9.84 |
| TEAOH, (Eastern Chemical) 35 wt. % in water | 183.74 |
| Al$_2$O$_3$ (Condea Pural SB) | 59.31 |
| H$_3$PO$_4$ (Acros), 85 wt. % in water | 100.63 |
| Water | 96.54 |

A mixture of the TEAOH and Ludox was heated for 12 hrs at 120° C. under autogenous pressure. After cooling this solution to room temperature, the phosphoric acid was added to this solution. After the solution was homogeneous, the Condea Pural SB alumina was added and the mixture was stirred until homogeneous. This mixture was then transferred to three 150 ml tubular stainless steel autoclaves, which were mounted on the axes of an oven. The autoclaves were rotated at a rate of 60 rpm. The oven was heated to 175° C. with a heating rate of 20° C./hr and kept at this temperature for 48 hrs. The mixture was stirred during the whole hydrothermal treatment at a tip-speed of 0.9 m/s. After cooling the product was washed and dried overnight at 120° C. According to XRD, the product was an intergrown phase of molecular sieves having AEI and CHA framework types with small amount of SAPO-5 with a particle size smaller than 100 nm as measured by SEM.

All patents, patent applications, test procedures, priority documents, articles, publications, manuals, and other documents cited herein are fully incorporated by reference to the extent such disclosure is not inconsistent with this invention and for all jurisdictions in which such incorporation is permitted.

When numerical lower limits and numerical upper limits are listed herein, ranges from any lower limit to any upper limit are contemplated.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains.

I claim:

1. A process for manufacturing a silicoaluminophosphate molecular sieve, said process comprising the steps of:
    (a) dissolving a silicon source into a solution containing a structure-directing template at conditions sufficient to establish a dissolved silicon concentration of at least 0.05 wt. %;
    (b) adding at least one aluminium source and at least one phosphorus source to at least a portion of the solution of step (a) to form a synthesis mixture, wherein at least the major portion of said aluminum source and phosphorus source are added to said solution after said solution has reached a dissolved silicon concentration of at least 0.03 wt. %; and
    (c) treating said synthesis mixture at a temperature sufficient to form said silicoaluminophosphate molecular sieve, wherein said silicoaluminophosphate molecular sieve comprises at least one intergrown phase of molecular sieves having AEI and CHA framework types, wherein said intergrown phase has an AEI/CHA mass ratio of from about 5/95 to 40/60 as determined by DIFFaX analysis.

2. The process of claim 1, wherein said solution of step (a) is substantially free of undissolved silicon source.

3. The process of claim 2, wherein said solution of step (a) has less than 0.01 wt. % of undissolved silicon source.

4. The process of claim 1, wherein step (a) is prior to step (b).

5. The process of claim 1, wherein step (c) further comprises an agitating step.

6. The process of claim 5, wherein said agitating step comprises at least one of a tumbling step or a stirring step.

7. The process of claim 1, wherein said conditions of step (a) comprise a temperature range, wherein said temperature range has a lower limit of about 50° C., and wherein said temperature range has an upper limit of about 5° C. lower then the decomposition temperature of said template.

8. The process of claim 1, wherein said template comprises tetraethylammonium hydroxide.

9. The process of claim 1, wherein said silicon source comprises an inorganic silicon compound.

10. The process of claim 9, wherein said inorganic silicon compound is a colloidal silica.

11. The process of claim 1, wherein said synthesis mixture has a composition of:

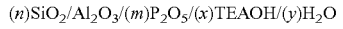

wherein the n has a range from about 0.005 to about 0.6, the m has a range from about 0.6 to about 1.2, the x has a range from about 0.5 to about 1.5, and the y has a range from about 10 to about 40.

12. The process of claim 1, wherein said synthesis mixture has a composition of:

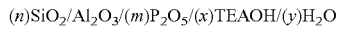

wherein the n has a range from about 0.01 to about 0.3, the m has a range from about 0.8 to about 1.1, the x has a range from about 0.8 to about 1.2, and the y has a range from about 10 to about 40.

13. The process of claim 1, wherein said silicoaluminophosphate molecular sieve has a particle size less than 600 nm.

14. The process of claim 1, wherein said silicoaluminophosphate molecular sieve has a particle size less than 100 nm.

15. The process of claim 1, wherein said intergrown phase has an AEI/CHA mass ratio of from about 7/93 to 38/62.

16. The process of claim 1, wherein said intergrown phase has an AEI/CHA mass ratio of from about 8/92 to 35/65.

17. The process of claim 1, wherein said intergrown phase has an AEI/CHA mass ratio of from about 9/91 to 33/67.

18. The process of claim 1, wherein the molecular sieve having CHA framework type is SAPO-34.

19. The process of claim 1, wherein the molecular sieve having AEI framework type is SAPO-18, ALPO-18 or a mixture of SAPO-18 and ALPO-18.

20. The process of claim 1, wherein said silicoaluminophosphate molecular sieve has an X-ray diffraction pattern having at least one reflection peak in each of the following ranges in the 5 to 25 (2θ) range:

| 2θ (CuKα) |
|---|
| 9.3-9.6 |
| 12.7-13.0 |
| 13.8-14.0 |
| 15.9-16.1 |
| 17.7-18.1 |
| 18.9-19.1 |
| 20.5-20.7 |
| 23.7-24.0. |

21. The process of claim 20, wherein said X-ray diffraction pattern has no reflection peak in the 9.8 to 12.0 (2θ) range.

22. The process of claim 20, wherein said X-ray diffraction pattern has no broad feature centered at about 16.9 (2θ).

23. The process of claim 20, wherein said reflection peak in the 17.7-18.1 (2θ) range has a relative intensity between 0.09 and 0.40 with respect to the reflection peak at 17.9 (2θ) in the diffraction pattern of SAPO-34, all diffraction patterns being normalised to the intensity value of the reflection peak in the 20.5-20.7 (2θ) range.

24. The process of claim 1, wherein said silicoaluminophosphate molecular sieve has the silica to alumina molar ratio ($SiO_2/Al_2O_3$) ranges from 0.01 to 0.28.

25. The process of claim 1, wherein said silicoaluminophosphate molecular sieve has the silica to alumina molar ratio ($SiO_2/Al_2O_3$) ranges from 0.02 to 0.20.

26. The process of claim 1, wherein said silicoaluminophosphate molecular sieve has the silica to alumina molar ratio ($SiO_2/Al_2O_3$) ranges from 0.03 to 0.19.

27. The process of claim 1, wherein the silicoaluminophosphate molecular sieve is subjected to the step(s) of one or more of the group consisting of: washing, cation exchange and calcining.

28. A silicoaluminophosphate molecular sieve manufactured by a process comprising the steps of:
(a) dissolving a silicon source into a solution containing a structure-directing template at conditions sufficient to establish a dissolved silicon concentration of at least 0.05 wt. %;
(b) adding at least one aluminium source and at least one phosphorus source to at least a portion of the solution of step (a) to form a synthesis mixture, wherein at least the major portion of said aluminum source and phosphorus source are added to said solution after said solution has reached a dissolved silicon concentration of at least 0.03 wt. %; and
(c) treating said synthesis mixture at a temperature sufficient to form said silicoaluminophosphate molecular sieve, wherein said silicoaluminophosphate molecular sieve comprises at least one intergrown phase of molecular sieves having AEI and CHA framework types, wherein said intergrown phase has an AEI/CHA mass ratio of from about 5/95 to 40/60 as determined by DIFFaX analysis.

29. The silicoaluminophosphate molecular sieve of claim 28 has a particle size less than 600 nm.

30. The silicoaluminophosphate molecular sieve of claim 28 has a particle size less than 100 nm.

31. The silicoaluminophosphate molecular sieve of claim 28, wherein said intergrown phase has an AEI/CHA mass ratio of from about 7/93 to 38/62.

32. The silicoaluminophosphate molecular sieve of claim 28, wherein said intergrown phase has an AEI/CHA mass ratio of from about 8/92 to 35/65.

33. The silicoaluminophosphate molecular sieve of claim 28, wherein said intergrown phase has an AEI/CHA mass ratio of from about 9/91 to 33/67.

34. The silicoaluminophosphate molecular sieve of claim 28, wherein the molecular sieve having CHA framework type is SAPO-34.

35. The silicoaluminophosphate molecular sieve of claim 28, wherein the molecular sieve having AEI framework type is SAPO-18, ALPO-18 or a mixture of SAPO-18 and ALPO-18.

36. The silicoaluminophosphate molecular sieve of claim 28, wherein said silicoaluminophosphate molecular sieve has an X-ray diffraction pattern having at least one reflection peak in each of the following ranges in the 5 to 25 (2θ) range:

| 2θ (CuKα) |
|---|
| 9.3-9.6 |
| 12.7-13.0 |
| 13.8-14.0 |
| 15.9-16.1 |
| 17.7-18.1 |
| 18.9-19.1 |
| 20.5-20.7 |
| 23.7-24.0. |

37. The silicoaluminophosphate molecular sieve of claim 36, wherein the X-ray diffraction pattern has no reflection peak in the 9.8 to 12.0 (2θ) range.

38. The silicoaluminophosphate molecular sieve of claim 36, wherein the X-ray diffraction pattern has no broad feature centered at about 16.9 (2θ).

39. The silicoaluminophosphate molecular sieve of claim 36, wherein the reflection peak in the 17.7-18.1 (2θ) range has a relative intensity between 0.09 and 0.40 with respect to the reflection peak at 17.9 (2θ) in the diffraction pattern of SAPO-34, all diffraction patterns being normalised to the intensity value of the reflection peak in the 20.5-20.7 (2θ) range.

40. The silicoaluminophosphate molecular sieve of claim 28 has the silica to alumina molar ratio ($SiO_2/Al_2O_3$) ranges from 0.01 to 0.28.

41. The silicoaluminophosphate molecular sieve of claim 28 has the silica to alumina molar ratio ($SiO_2/Al_2O_3$) ranges from 0.02 to 0.20.

42. The silicoaluminophosphate molecular sieve of claim 28 has the silica to alumina molar ratio ($SiO_2/Al_2O_3$) ranges from 0.03 to 0.19.

43. A process for the conversion of an oxygenate to olefins in a reactor, the process comprising the steps of:
  (i) contacting the oxygenate under catalytic conversion conditions with the silicoaluminophosphate molecular sieve made by a process comprising the steps of:
    (a) dissolving a silicon source into a solution containing a structure-directing template at conditions sufficient to establish a dissolved silicon concentration of at least 0.05 wt. %;
    (b) adding at least one aluminium source and at least one phosphorus source to at least a portion of the solution of step (a) to form a synthesis mixture, wherein at least the major portion of said aluminum source and phosphorus source are added to said solution after said solution has reached a dissolved silicon concentration of at least 0.03 wt. %; and
    (c) treating said synthesis mixture at a temperature sufficient to form said silicoaluminophosphate molecular sieve,
    wherein said silicoaluminophosphate molecular sieve comprises at least one intergrown phase of molecular sieves having AEI and CHA framework types, wherein said intergrown phase has an AEI/CHA mass ratio of from about 5/95 to 40/60 as determined by DIFFaX analysis; and
  (ii) withdrawing the olefins from the reactor.

44. The process of claim 43, wherein said oxygenate comprises at least one of methanol, ethanol, n-propanol, isopropanol, $C_4$-$C_{20}$ alcohols, methyl ethyl ether, dimethyl ether, diethyl ether, di-isopropyl ether, formaldehyde, dimethyl carbonate, dimethyl ketone; acetic acid, and any combination thereof.

45. The process of claim 43, wherein said oxygenate is methanol.

* * * * *

UNITED STATES PATENT AND TRADEMARK OFFICE
CERTIFICATE OF CORRECTION

PATENT NO. : 7,459,136 B2
APPLICATION NO. : 11/221192
DATED : December 2, 2008
INVENTOR(S) : Machteld M. Mertens It is certified that error appears in the above-identified patent and that said Letters Patent is hereby corrected as shown below:

Title page, item [73] Assignee: should read as follows:
ExxonMobil Chemical Patents Inc., Signed and Sealed this Twenty-fourth Day of March, 2009

JOHN DOLL
*Acting Director of the United States Patent and Trademark Office*